(12) United States Patent
Neister (10) Patent No.: US 8,753,575 B2
(45) Date of Patent: Jun. 17, 2014

(54) METHOD AND APPARATUS FOR STERILIZING AND DISINFECTING AIR AND SURFACES AND PROTECTING A ZONE FROM EXTERNAL MICROBIAL CONTAMINATION

(76) Inventor: S. Edward Neister, New Durham, NH (US)

( * ) Notice: Subject to any disclaimer, the term of this patent is extended or adjusted under 35 U.S.C. 154(b) by 746 days.

(21) Appl. No.: 11/831,667

(22) Filed: Jul. 31, 2007

(65) Prior Publication Data

US 2010/0028201 A1     Feb. 4, 2010

(51) Int. Cl.
*A62B 1/08* (2006.01)
*B01D 39/00* (2006.01)
*B01D 41/00* (2006.01)
*B01D 46/00* (2006.01)
*B01D 49/00* (2006.01)
*B01D 50/00* (2006.01)
*B01D 53/14* (2006.01)
*B01D 51/00* (2006.01)

(52) U.S. Cl.
USPC ............................................. 422/121; 96/224

(58) Field of Classification Search
USPC ............................................. 96/224; 422/121
See application file for complete search history.

(56) References Cited

U.S. PATENT DOCUMENTS

| | | | | |
|---|---|---|---|---|
| 3,672,126 A * | 6/1972 | Goettle | ............................. | 96/18 |
| 4,317,041 A | 2/1982 | Schenck | | |
| 4,458,153 A | 7/1984 | Wesley | | |
| 4,524,079 A | 6/1985 | Hofmann | | |
| 5,364,645 A | 11/1994 | Lagunas-Solar et al. | | |
| 5,492,676 A * | 2/1996 | Katatani et al. | ............... | 422/168 |
| 5,505,904 A * | 4/1996 | Haidinger et al. | ............... | 422/24 |
| 5,750,072 A | 5/1998 | Sangster et al. | | |
| 5,753,106 A | 5/1998 | Schenck | | |
| 5,843,374 A | 12/1998 | Sizer et al. | | |
| 5,993,738 A * | 11/1999 | Goswani | ........................... | 422/22 |
| 6,099,799 A | 8/2000 | Anderson | | |
| 6,149,717 A * | 11/2000 | Satyapal et al. | ................... | 96/16 |
| 6,235,090 B1 * | 5/2001 | Bernstein et al. | ................. | 96/57 |
| 7,326,387 B2 | 2/2008 | Arts et al. | | |
| 2004/0120846 A1 * | 6/2004 | Bates et al. | ....................... | 422/4 |

(Continued)

FOREIGN PATENT DOCUMENTS

| | | |
|---|---|---|
| CN | 2139811 Y | 8/1993 |
| CN | 2604181 Y | 2/2004 |
| CN | 2662909 Y | 12/2004 |
| JP | 2003207165 A | 7/2003 |
| KR | 20040097758 A | 11/2004 |
| WO | 0028552 A1 | 5/2000 |
| WO | 0238447 A2 | 5/2002 |
| WO | 0245756 A2 | 6/2002 |
| WO | 02078754 A1 | 10/2002 |
| WO | 2005061396 A1 | 7/2005 |

*Primary Examiner* — Walter D Griffin
*Assistant Examiner* — Christopher K Vandeusen
(74) *Attorney, Agent, or Firm* — Lambert & Associates; Gary E. Lambert; David J. Connaughton, Jr.

(57) ABSTRACT

This invention relates to a method, process and apparatus for disinfecting and sterilizing all types of surfaces contaminated with microorganisms and toxic substances to render both inactive. Furthermore, this invention relates to both a method and apparatus for disinfecting and/or sterilizing breathable air and then using this air to protect a confined space from external contamination. The apparatus consists of a new ultra-violet (NUV) source that is more effective than mercury based 254 nm light for destroying DNA of virus, bacteria, spores and cists. It is most effective in breaking chemical bonds in toxic gases and Biotoxins that are useful to terrorists. It is combined with other apparatus that remove particulates and byproducts sometimes produced by the NUV source and maintains positive pressure of the confined space so as to prevent the influx of air from outside the protected zone.

6 Claims, 10 Drawing Sheets

(56) References Cited

U.S. PATENT DOCUMENTS

| | | | |
|---|---|---|---|
| 2004/0120850 A1* | 6/2004 | Kaiser | 422/22 |
| 2004/0166018 A1 | 8/2004 | Clark et al. | |
| 2005/0173652 A1* | 8/2005 | Ressler | 250/455.11 |
| 2006/0188835 A1 | 8/2006 | Nagel et al. | |
| 2007/0045561 A1* | 3/2007 | Cooper | 250/453.11 |

* cited by examiner a. NUV Lamp b. Directed Radiation

Figure 1: NUV Source

Figure 2: Volumetric Air Treatment a. floor Treatment & Cleaner b. Handheld Surface Treatment

Figure 3: Surface Treatment a. Unprepared Food b. Serving Counter

Figure 4: Food Treatment

Figure 5: Zone Air Purifier & Sterilizer

Figure 6: Operating Zone with Sterilizer

Figure 7: CFD Air Flow

Figure 8: Dimer Formation by UV Photon
(by permission of ERG @ UNH)

Figure 9: UV Absorption of DNA

Figure 10: B. coli @ 0.8u absorption

Figure 11: UV Irradiation Test on MS2

Figure 12: UV dose required for 4 log (99.99%) deactivation

Figure 13: ESP range of effectiveness

Figure 14: Sterilray Technology Test Data

Figure 15: 300x and 100x micrographs of Bacillus atrophaeus

METHOD AND APPARATUS FOR STERILIZING AND DISINFECTING AIR AND SURFACES AND PROTECTING A ZONE FROM EXTERNAL MICROBIAL CONTAMINATION

BACKGROUND

1. Field of the Invention

This specification teaches a new method for disinfecting and sterilizing air, surfaces of all types and food from microorganisms and toxic chemical substances. More particularly, it relates to a process and apparatus for protecting surfaces in closed or captured environments (zones) from external sources of microbial contamination in an efficient and cost effective process. These zones can be large volumes such as high rise building, cruise ships and jet airliners, or small volumes such as small rooms or surgical operation areas whether in a hospital operating room or on the battle field.

2. Description of the Related Art

All prior art for sterilizing and disinfecting air has been based on using commercially available ultra-violet (UV) lamps or by using magnetic fields. These lamps are either pulsed or continuous. Continuous lamps are mercury based and emit principally at 254 nm. A number of companies are presently producing UV light based apparatus for the destruction of virus, bacteria, spores and pathogens (microorganisms or VSP) that are in room air. This is an effective treatment because it continually exposes room air currents to the treatment light and over time has sufficient exposure time to treat VSP's. The required exposure times range from 10's to 100's of seconds, depending on the light absorption capability of the different virus and bacteria at the 254 nm. While this is effective for treating the room air of individual rooms, it requires long treatment times to be effective for treating large flowing volumes of air that pass quickly down large ducts. Long treatment time is impractical for treating most surfaces.

Magnetic based apparatus also require time to deactivate or destroy these VSP's. Two such inventions are directed to specific applications. Wesley, U.S. Pat. No. 4,458,153 is directed specifically towards liquid like substances enclosed in pipes, but does not discuss any test results. Sangster, U.S. Pat. No. 5,750,072 requires an injection of a sterilizing fluid as a mist or vapor for the magnetic field to produce radicals that in turn are used to alter the VSP's. He does not discuss any test results. Hofmann, U.S. Pat. No. 4,524,079 is directed specifically to treating food stuffs. He speaks of requiring up to 100 pulses at frequencies ranging from 5 to 500 kHz. None of these patents are admitted to being prior art by their mention in this background section. Although the action time would be short, the power required to treat large areas and the apparatus design limit its practical application.

The broad ultraviolet spectrum had been divided into three regions depending on its different effects on biological systems. Reference to these regions are predominantly made in medical terminology with UV-A defined as a range or band between 320 nm and 400 nm, UV-B defined as a band between 280 nm and 320 nm, and UV-C defined as encompassing wavelengths shorter than 280 nm. Photochemists and photobiologists do not generally use these terms because absorption spectra of chemical bonds are much narrower than these generally defined bands. Instead, they use the wavelength of the applied radiation to correlate the observed effects.

Claims have been made that germicidal UV-C radiation is used to deactivate DNA. This is because the mercury lamp emission at 254 nm is close to a good DNA absorption band. None of these claims make reference to any shorter wavelengths and to the primary DNA protein absorption band that peaks at 200 nm (see FIG. 9). In fact, all literature directs researchers away from using any shorter wavelengths due to the high absorption of molecular water. Mercury lamps are used for wastewater treatment and work well for this application. However, this specification teaches that since we do not live underwater, the protein absorption band offers much more significant action spectra that can be used to kill and deactivate the DNA of microorganisms more effectively. This concept is a significant advancement and a step change in the technology used for sterilization and disinfection.

During the past few years, new UV emitting lamps based on the excitation of excimers are becoming commercially available. These emitters produce single line or narrow spectral emission at a wavelength determined by the gas composition of the lamp. If the treatment lamp's wavelength is chosen to match closely to the peak of absorption of the microorganism's DNA, then a lethal dosage can be delivered to the VS P's in a shorter time. No patent has been found that teaches the use of new ultra-violet (NUV) sources coupled with supporting equipment that can effectively and efficiently disinfect and sterilize large volumes of air, large and small surfaces, and food stuffs in various stages of preparation.

In this specification, sterilization or sterilize refers to sterilization or high level disinfectant as defined by US FDA. The terms disinfectant and disinfection refers to all other levels of disinfection.

NUV Background

The genetic makeup of all living organisms is contained in their DNA molecule. Replication occurs by the splitting of the DNA molecule, which duplicates itself through a transformation of its structure. Parts of the DNA molecule have been given names such as pyrimidine bases, cytosine, thymine or uracil that form a group of biochemicals that sustain life. The long DNA molecule holds itself together by using simple bonds like those found in sugars.

Figure 8:
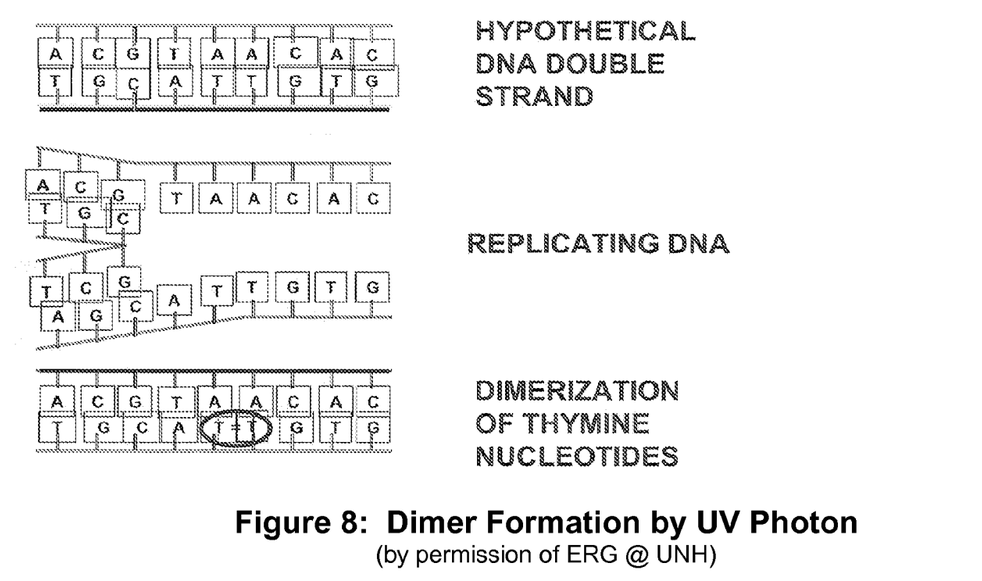
FIG. 8 is a graphic showing dimer formation in a DNA molecule.

Researchers believe that the energy of the germicidal UV photon causes the formation of a strong (covalent) bond to develop between specific biochemicals. However, the bond strength of the covalent bond is very dependent on the relative position of the participating atoms. When the bond is symmetrical on both sides of a hydrogen atom in the bond, it is referred to as a dimer. A dimer is a very strong bond and is not generally broken during the vaporization of the liquid. Germicidal UV light is known to produce Thymine, cytosine-thymine, and cytosine dimers. After the formation of the dimer, further replication of the DNA stops. FIG. 8 shows the concept of the dimer formation in a DNA molecule.

Figure 9:
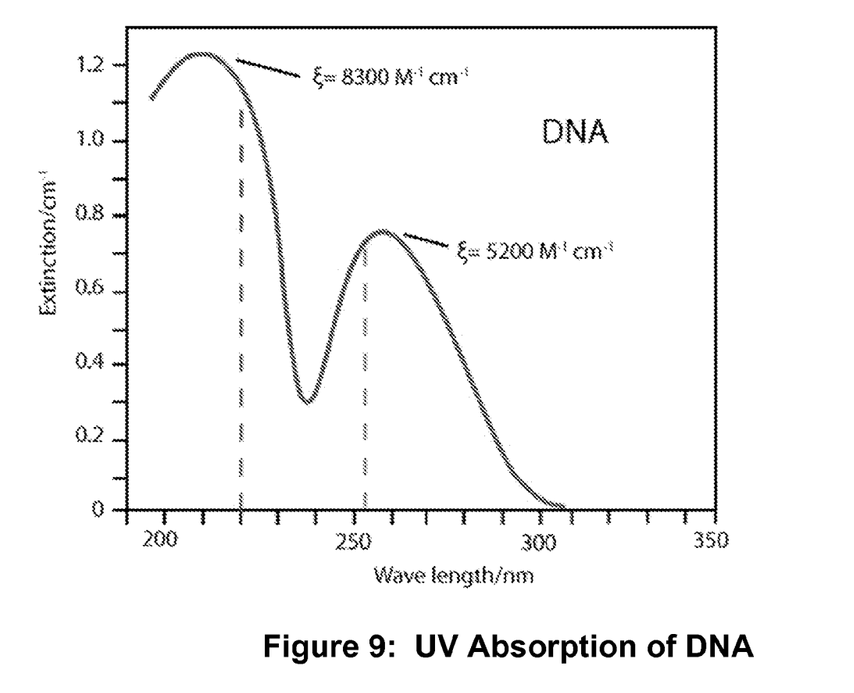
FIG. 9 is a graph plotting UV absorption of DNA according to wavelength.

The DNA molecule absorbs light from about 180 nm to about 4300 nm. The most effective wavelength in water is about 254 nm because water absorption increases steadily as the wavelength decreases below 240 nm. DNA absorption also increases with lower wavelength. FIG. 9 graphically shows this relationship (Von Sonntag; Disinfection by free radicals and UV-radiation. Water Supply 4, 11-18 (1986)).

The commercial germicidal light source for UV irradiation near the 260 nm absorption peak of DNA has been produced by using mercury as the source for generating photons. The mercury gas and its pressure in the lamp determine the wavelength of the emitting light. For low-pressure (LP) and low-pressure high output (LPHO) lamps, the emitting wavelength is 254 nm. For medium pressure lamps, the emission ranges from 200 nm to above 300 nm. However, the strength of the emitted light is not effective below 245 nm for the continuous emitting lamps and below 235 nm for medium pressure lamps. Xenon gas in pulsed lamps produces a similar emission as the medium pressure mercury lamps.

DNA action spectra show that absorption increases as the wavelength decreases, with a relative maxima at 260 nm and largest at 200 nm. Many articles indicate the principal action spectra of the DNA absorption is from 245 to 280 nm range and do not address the 200 nm peak. Since water absorption significantly increases below 235 nm, it becomes apparent that DNA effectiveness curves that omit the 200 nm peak apply only to organisms in water.

Figure 10:
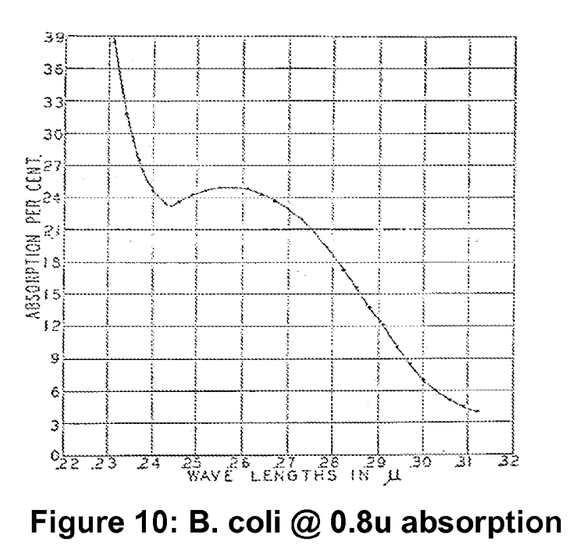
FIG. 10 is a graph plotting DNA absorption without the influence of water.

MS-2 Phage is a marker virus that is used to measure reproduction viability after germicidal UV irradiation. FIG. 10 is DNA absorption without the influence of water (Gates, F. L. A study of the bactericidal action of ultra violet light III. Jour. General Physiology 14, 31-42 (1930)). Absorption is more than doubled at 222 nm.

A recent technical paper (Peak et al, UV action spectra for DNA dimer induction. Photochemistry and Photobiology, 40, 5 (613-620), 1984) suggests that dimer formation is not the only requirement to inactivate DNA. Absorption of other molecular groups in the long DNA chain increase as the wavelength is reduced from 254 nm. Damaging or destroying these bonds may be more effective in deactivating the DNA than compared to the 254 nm band. No one has done a detailed study of the effectiveness of inactivation for the different single line UV emitters that are produced by the new UV source (NUV) excimer lamps. Reports show that damage caused by 254 nm light can be reversed by longer wavelength UV and blue light (FIG. 12). 222 nm photons with their higher energy are not expected to cause this 'photo-reactivation' phenomenon. However, this theory needs to be confirmed.

An excimer lamp emitting at 222 nm is considered the most effective source because DNA chains and biochemicals have greater absorption at this wavelength. The steep rise in absorption below 250 nm is exhibited by all proteins and most nitrogenous bases. It has been fairly well established that the peptide bonds are responsible for the steep rise in absorption exhibited by all proteins. A similar increase in absorption at lower wavelengths occurs as well for nucleo-proteins, aromatic amino-acids, diglycine, triglycine, and bovine albumin (McLaren, et al, Photochemistry of Proteins and Nucleic Acids, Pergamon Press, Macmillan Company, 1964). An organic chemist suggests that this lower wavelength is more effective in breaking bonds and producing dimers in the purine bases and sugar phosphates instead of the pyrimidines. The 222 nm is not strongly absorbed by water vapor and oxygen in the air. A shorter wavelength would be most certainly rendered ineffective by water vapor and oxygen absorption for long irradiation distances in air. Shorter wavelength radiation would significantly increase the production of ozone that is harmful to humans and animals.

Tests

Using a lamp that emits 222 nm, a comparison test with and without water was made to determine the effect of this radiation on organisms. The organism used in all tests was the MS-2 virus, which has become a standard indicator of mutation effectiveness. The EPA report (811-R-96-002) reports a 4.3 average log reduction of the MS-2 virus using mercury light 254 nm at an irradiance greater than 128 mj/cm$^2$.

Three wavelengths were tested: 222, 253, 259 nm. The 222 nm lamp was tested at three levels of irradiance with the virus in a thin layer of water in order to reduce the absorption effect of water. A separate test was also done with the virus in more water. The 253 and 259 nm lamps were tested at the identical irradiance levels with the virus in water. Controls were made on all tests and a single test dish on each lamp was made to check experimental error.

Figure 11:
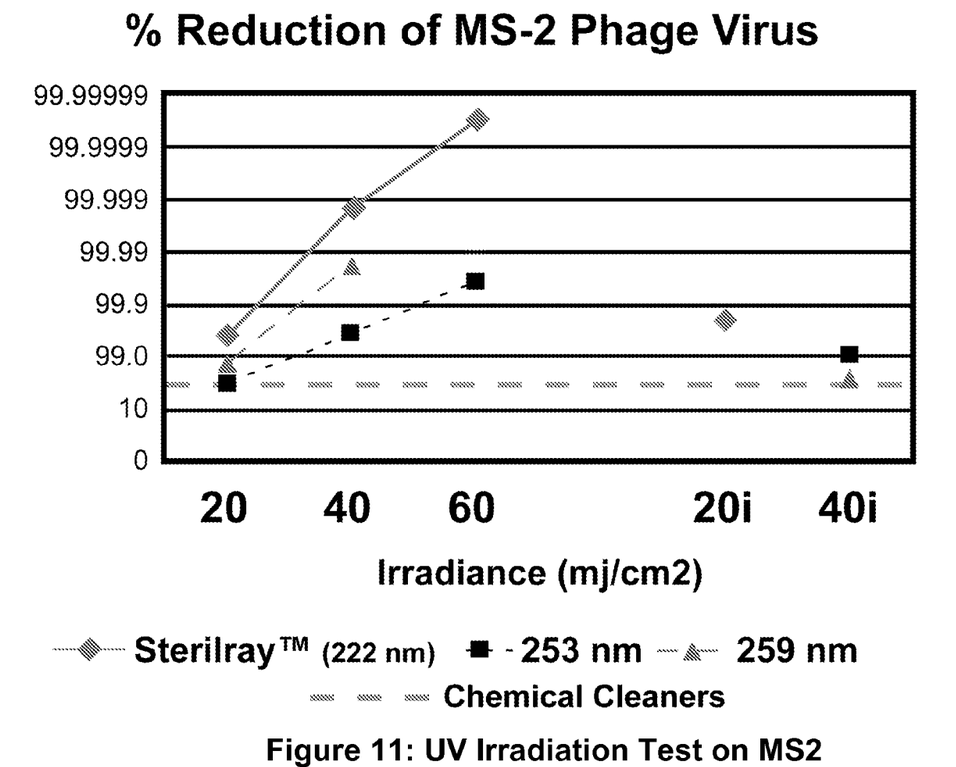
FIG. 11 plots the effectiveness for reduction of the MS-2 phage virus by different wavelengths of UV radiation.

The 222 nm lamp (FIG. 11) produced log 5 reductions at 40 mj/cm$^2$ and log 6.5 reductions at 60 mj/cm$^2$. The water test produced a 3.2 log reduction, which matched the equivalent calculated irradiance in air. The 253 and 259 nm lamps produced about log 4 reductions at 60 mj/cm$^2$. A 3 million reduction in population is about 10 to 100 times more effective than reported mercury 254 nm results at the same irradiance.

Analysis

The results of the test indicate that 222 nm light is very effective in causing mutations in organisms. These tests indicate an improvement of between 10 to 1000 times, depending on the intensity of the lamp. It is important to note the improvement of the 259 nm source compared to the 254 nm source. It produced a 10 times improvement in the test sample. This improvement illustrates the importance in using a UV photon emitter that is near the absorption peak of the DNA or targeted chemical such as nitrogenous bases, proteins, nucleic acids, or amino-acids.

It is important to note that DNA biochemicals will have different absorption spectra and the peak absorption will be shifted by water, pH, temperature, previously absorbed light and surrounding contaminates in the air. The presence of ozone can significantly reduce the resistance to damage and shorten the action kill time. For some applications, ozone is produced to improve the killing or deactivating efficiency.

For example, tyrosine has a relative maximum at 275 nm, a red shift of 20 nm from the normal DNA curve. The tobacco mosaic virus peaks at 265 nm, but its X-protein at pH 7.3 peaks at 280 nm while the RNA peak occurs at 260 nm. Critical to the destruction of the organism is targeting the proper biochemical so the critical dosage can be delivered in the shortest time. The critical dosage is that dosage that destroys or deactivates the organism and prevents its replication.

The excimer lamp is a coaxial design that can be made as small as a pencil to as large as 1 meter long. Lamp efficiency is about the same as mercury at 10-25% wall power to UV emission. The design has several advantages over mercury lamps. Most important is that its gas can be chosen to maximize its emission to the absorption peak of the targeted biochemical. Unlike the mercury lamp, the excimer intensity can be varied from near zero to maximum. It will produce 10 to 1000 times more intensity than mercury, depending on the lamp dimensions, and it does not use mercury that will soon become regulated by the EPA.

The energy of the emitted photon is determined by its wavelength. Photon energy is about 5 ev at 250 nm and increases for shorter wavelengths. Different bonds in the DNA will be affected with photons of different energy.

Figure 12:
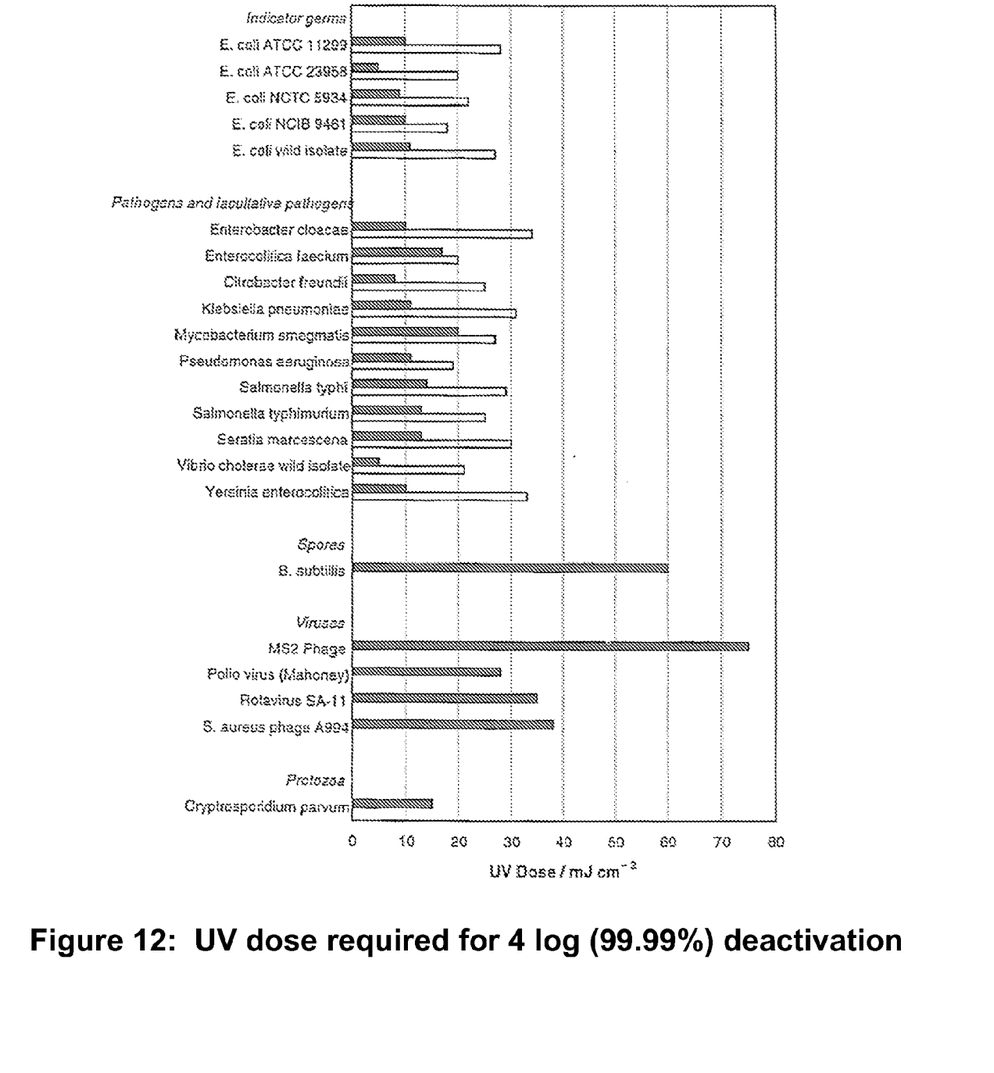
FIG. 12 plots the UV dose required to achieve a four log deactivation of selected microbes using 254 nm UV light.

FIG. 12 illustrates the 254 nm dose required to deactivation different VSP's. The bars represent with (solid) and without (open) photo-reactivation. Note that a dose of 75 mj/cm$^2$ is required to deactivate the MS2 Phage virus and prevent photo-reactivation. In the tests shown in FIG. 11, half the dose at 222 nm was just as effective as the higher dose at 254 nm. Even though the sample was under water, the 222 nm radiation was still more effective than 254 nm radiation.

The 222 nm photon has more energy and is absorbed by S—N, S—O, O—O, O—H, and many carbon bonds that do not absorb 254 nm. This suggest that 222 nm light may also prevent DNA repair that has been reported for low level 254 nm UV sources.

Toxic Gas Weapons

Biotoxins and nerve agents can be used by terrorists as weapons against groups of people. Nothing economical has been developed that could mitigate an attack and prevent the loss of life and incapacitation at the point of attack. While government agencies of the US have developed detectors that could be used in the future to warn people in the confined areas that are under attack, nothing would prevent the attack from being effective.

Biotoxins and nerve agents are organic molecules that contain either DNA or have long chain carbon based molecules. Both of these are susceptible to destruction using NUV light sources. 222 nm will destroy the C=C and C=O bonds causing the destruction of the chemical.

The most effective means for delivery of these agents is to spread them in a gas phase through the air ventilation system. A detector would be used to turn on sufficient NUV sources so that the agents are destroyed before exiting the ventilation system into the confined area where the captured population is present. Tests still need to be done in regulated and controlled laboratories to develop the criteria for these sources to be effective and become the first line of defense. However, the concept of using the NUV source as well as the associated support equipment used for treating VSP's is valid and is also contained in the scope of this specification.

Support Equipment Contained in the Apparatus

Figure 13:
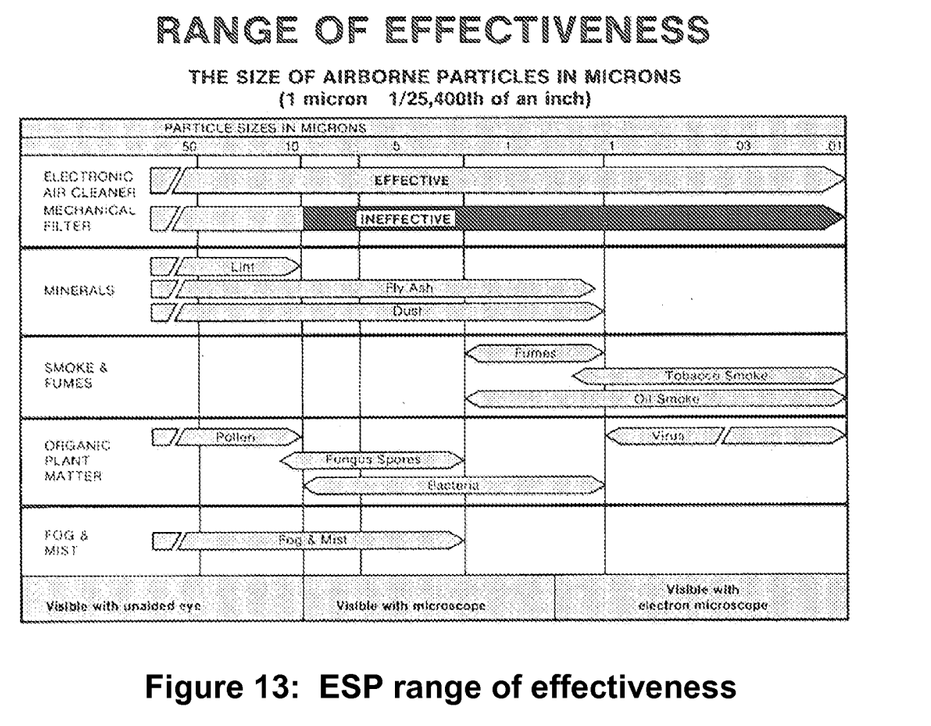
FIG. 13 is a graphic comparing the range of effectiveness of various filters for removing airborne particles.
Figure 14:
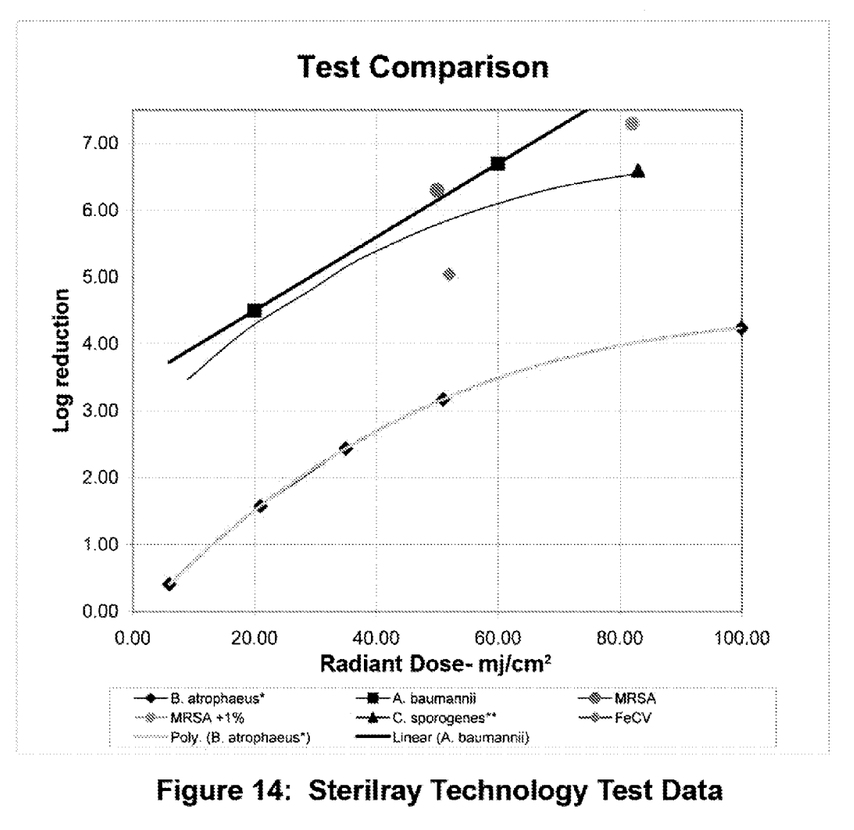
FIG. 14 is a graph comparing tests of different pathogens for log reduction for different radiant dosages of NUV light.
Figure 15:
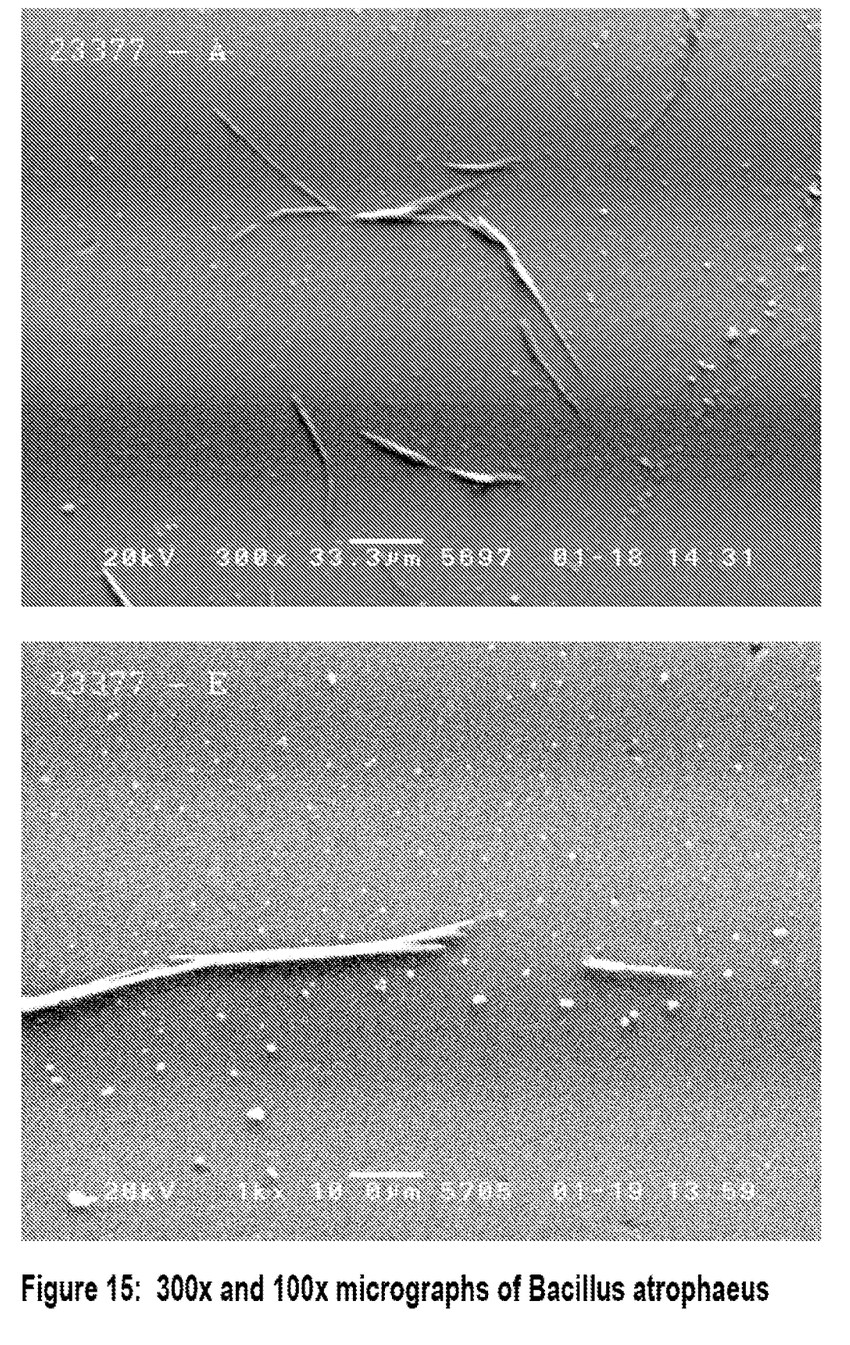
FIG. 15 is a low power exposure at 300× and 1000× micrographs of the Bacillus atrophaeus organism after receiving a radiant dose from the NUV light source.

Important to the sterilization and disinfecting apparatus is the use of a high E field electrostatic precipitator (ESP). FIG. 13 compares the range of effectiveness with mechanical filters for different pollutant sizes. As illustrated in the fourth column, it is capable of removing VSP's. However, since it can also capture fog and mist, it has the ability to breakdown ozone $O_3$ into oxygen. Its use prevents levels of ozone from exceeding the EPA exposure safe levels.

The apparatus includes a humidification system to provide and maintain minimum moisture content at predetermined and controllable levels. In addition, the apparatus contains baffles and zone restriction devices that enhance the zone protection and minimize the positive pressure required to maintain the protected zone.

SUMMARY OF THE INVENTION

Critical to this method is the development of a new ultraviolet (NUV) source that emits single line photons that correspond to the maximum absorption band for DNA. The preferred embodiment is a NUV source at 222 nm. This spectral emission is $10^4$ times more effective than standard 254 nm photons for stopping DNA replication. Action times are reduced from 10's to 100's of seconds to times less than 0.1 seconds. Photon energy of the NUV source is sufficiently high to break carbon bonds of chemical toxic substances with similar action times. Unique to obtaining short action (kill) times is a determination of the specific wavelength required to destroy the targeted organism or chemical. The NUV source is chosen to supply the single line emission that matches the peak absorption of the targeted organism or chemical.

This makes for a cost effective method for sterilizing and disinfecting air, surfaces and food during normal daily activity, preventing the previous need to restrict occupation and use of areas being treated. Furthermore, the apparatus is capable of effectively and efficiently disinfecting floors, hand rails, objects that are in constant contact with transient populations for the purpose of preventing transmission of disease and toxic substances that can cause injury or illness to these populations. The NUV radiation can be applied to any object or surface that needs to be disinfected and/or sterilized. Testing will also determine the correct exposure limits to prevent any harmful effects that could occur when used to disinfect human skin, hands, animal surfaces such as skin, fur, and hair, and critical plastics and materials used in medical devices, Because the NUV source is a light source, it can be directed to expose different levels of thick materials by using light conducting fibers to distribute the light intensity. An example would have the NUV source disinfecting a floor by directing it at the floor while some of the light is directed to the bottom of a rug or floor scrubbing brush by light fibers imbedded in the brush. In a similar manner, products that have cavities or areas not exposed directly by the external source could be disinfected.

The NUV source can be used to directly disinfect room surfaces or particles and microbes in the room air by directly exposing all objects for the required exposure time. Several sources can be combined to assure exposure to all surfaces and to reduce total exposure time. Rooms contaminated by bioterrorist agents could be treated by moving the NUV source(s) in many directions and moving it (them) around the room during treatment.

Normal breathable air contains many contaminates including moisture droplets, dust, lint, bacteria, virus, cists, spores and possible toxic gases. The NUV source can be used by itself to disinfect air. Sterilization sometimes requires the removal of all particles to the smallest possible size. The NUV source can produce byproducts that must be removed for some treatment applications. These byproducts include oxidized air (ozone), condensable chemical byproducts, and damaged microorganisms. Critical to the apparatus is the removal of these contaminates and byproducts. In some special applications, ozone is added to make treatment more effective. Consequently, the apparatus includes high E field precipitators, ozone generators and ozone destroying light and apparatus to make effective use of the combination of these technologies.

Sterilized air is then used to prevent microbial contamination of a protected zone by preventing the influx of untreated air from outside this zone. The apparatus includes pressurizing equipment and zone baffles that provide sufficient outflow from the protected zone so as no contamination can occur. Protected zones can be as small as a wound area on a battlefield operating table to a cruise ship, airplane, or high rise building with thousands of inhabitants.

A major source of infection and terrorist's activity is directed at food and material handling. Photon emitters have been used to effectively clean food stuffs and surfaces for many years. However, this invention uses the NUV source that makes it cost effective in treating surfaces of food and materials since the action time is almost immediate. The apparatus of this invention is capable of irradiating foodstuffs in conveyor assemblies, stationary carts and in handling routes during the movement from storage to food preparation processes. It can also be used to sterilize/disinfect medical or critical parts on an assembly line prior to packaging.

DESCRIPTION OF THE PREFERRED EMBODIMENTS

Figure 1:
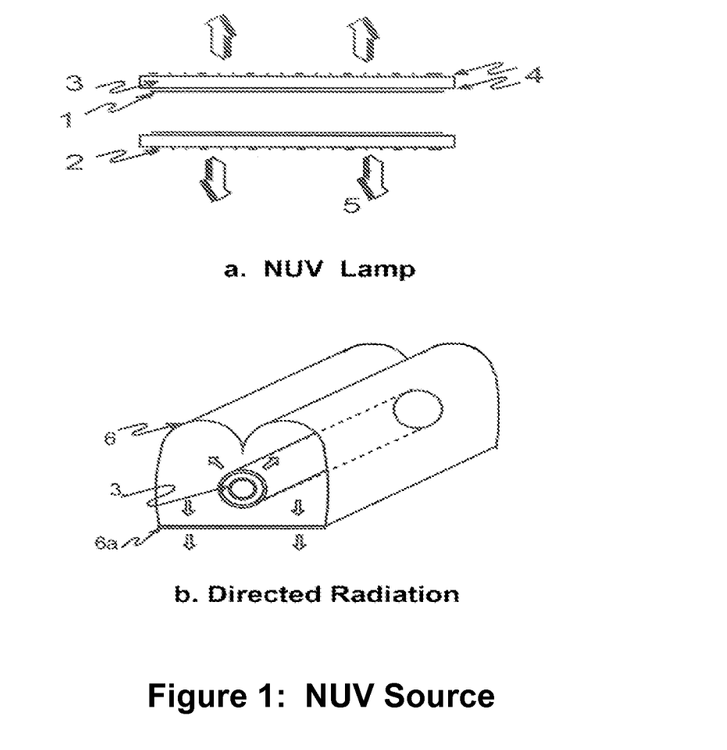
FIG. 1 is a perspective schematic view of a preferred embodiment of the present invention defining the location of important components of the NUV source therein.

The drawings illustrate the invention in its different forms and the apparatus required for sterilization or disinfection of air and surfaces that contain VSP's. FIG. 1 illustrates the NUV light source. FIG. 1a shows the NUV source. The high voltage electrode 1 is located inside the inner tube of the annular lamp. The ground electrode screen 2 is located on the outside of the annular lamp. The gas that produces the UV photons is located in the annular region 3 between the inner and outer tubes 4. The gas type is chosen so that the emitted UV photons are absorbed by the targeted microorganism or chemical. The preferred embodiment is 222 nm but could also be 282 nm. UV radiation is emitted radially outward 5. Changing the voltage or current between the two electrodes changes the amount of UV radiation that is produced.

FIG. 1b illustrates the NUV light source used to direct the UV photons towards a specific location, direction, surface, material or substance. The NUV source is shown in the center of the drawing as an end view. The specialized reflector 6 end view incorporates a specialized 'gull wing' design so that >90% of the emitted light is directed to the planar surface below. The specialized reflector 6 also incorporates barium sulfate ($Ba_2SO_4$) as the reflective material in order to maximize the number of photons that are reflected onto the planar surface. In some cases, a cover 6a is necessary to protect the NUV source and reflector from dirt. This cover is transparent to 222 nm and 282 nm light. The specialized reflector can also have different shapes that change the directed radiation for different applications.

This design provides a convenient method and apparatus to disinfect commonly touched objects that act as fomites to transmit pathogens from one person to the next. It would also provide a means for wound treatment prior and post surgery and for the treatment of chronic wounds. It is also provides a means to disinfect hospital and health care rooms, operating tables, hand rails and equipment surfaces that support patient care.

Furthermore, in cases of critical shortages of gloves, robes and masks, the NUV source can be used in this manner to disinfect periodically when appropriate instead of retrieving new ones from supply.

The NUV source(s) can also be used to disinfect patient examining tools, records, pens and equipment between patients. Everything that is brought into the room for examining the patient should be put through the medical caddie after exiting the room and retrieved only after changing gloves and/or garments.

In use, the NUV source can be made to any size and length. In air ducts, the embodiment shown in FIG. 2 item 6b would have the NUV source supported from the side, top or bottom of the duct so that its irradiation travels parallel to the airflow. For unique applications, a second embodiment FIG. 5 item 16 would have the NUV source and cylinder reflector supported inside the duct so that irradiation is perpendicular to the airflow. An example of this embodiment would be a NUV source positioned in the center of a tumbling dryer. All garments or objects or food stuffs would be irradiated during the drying or tumbling process for a length of time that would guarantee a high level of disinfection.

Figure 2:
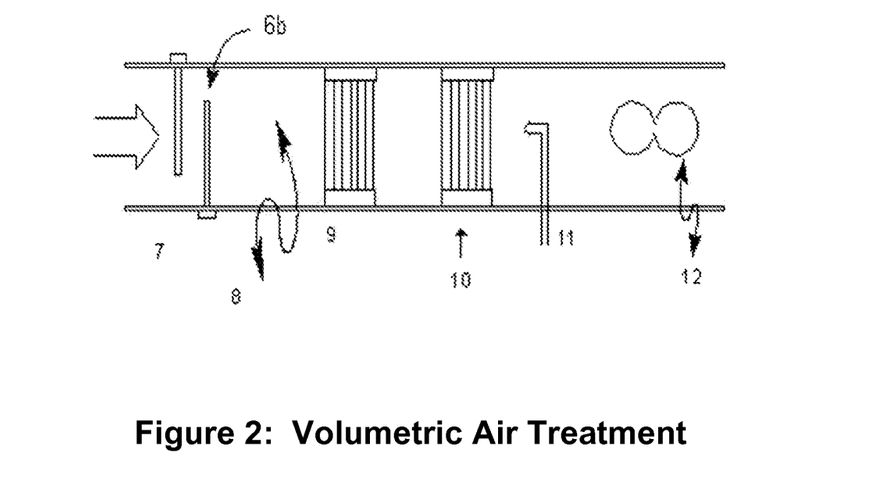
FIG. 2 is a perspective schematic view of a preferred embodiment of the present invention defining the location of important components for disinfecting or sterilizing large volumes of air therein

FIG. 2 illustrates the apparatus required for the disinfection and sterilization of airflow inside a large duct. NUV sources 7 precede an electrostatic precipitator (ESP) 9 by some distance 8 that permits a short action time to complete the destruction of the toxic gases or VSP's. A humidifier 10 may follow the precipitator with control sensors 11 so that the humidity of the exiting air can be selected and maintained. A fan(s) 12 may also be used to pressurize the exiting air so that a slight pressurization can be applied to a protected zone to prevent contaminated air from entering. Depending on the nature of the zone, restricting baffles (not shown) are used to assist in maintaining a positive pressure inside the protective zone.

Figure 3:
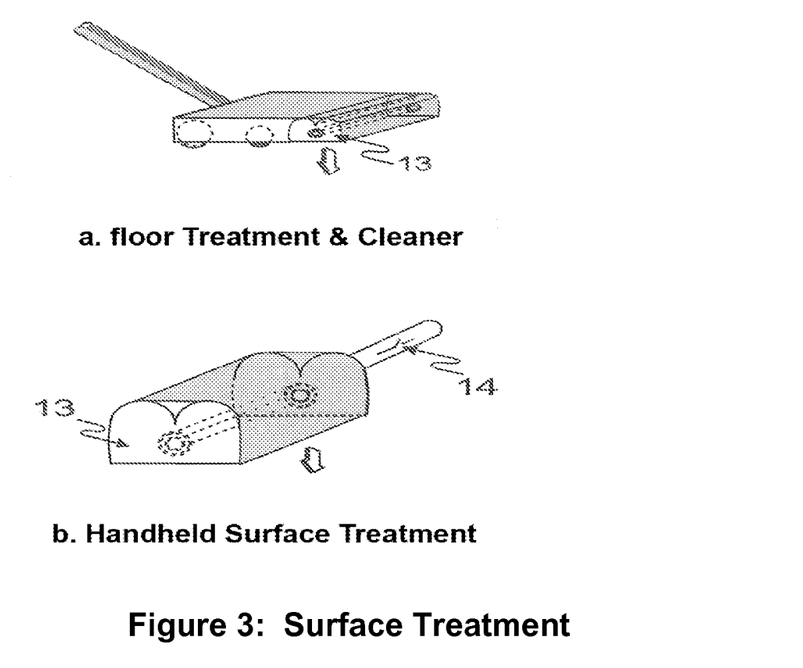
FIG. 3 is a perspective schematic view of a preferred embodiment of the present invention defining the location of important components for disinfecting floor surfaces and other surfaces such as chairs, hand rails, counter tops, trays, table tops and the like therein.

FIG. 3a illustrates the NUV source 13 located inside the forward compartment of a vacuum cleaner or floor cleaning machine. The vacuum cleaner can be either a standup floor model or a canister model. It could also be any device that would support and carry the NUV source close to the floor. The significant part is that the NUV source with reflector 6 consists of the components as described in FIG. 1b. FIG. 3b illustrates a preferred embodiment with the NUV source contained in a hand held wand. Sensing switches 14 can be included in this embodiment that shut off the NUV source when the wand is not directed correctly to the desired treatment surface.

Figure 4:
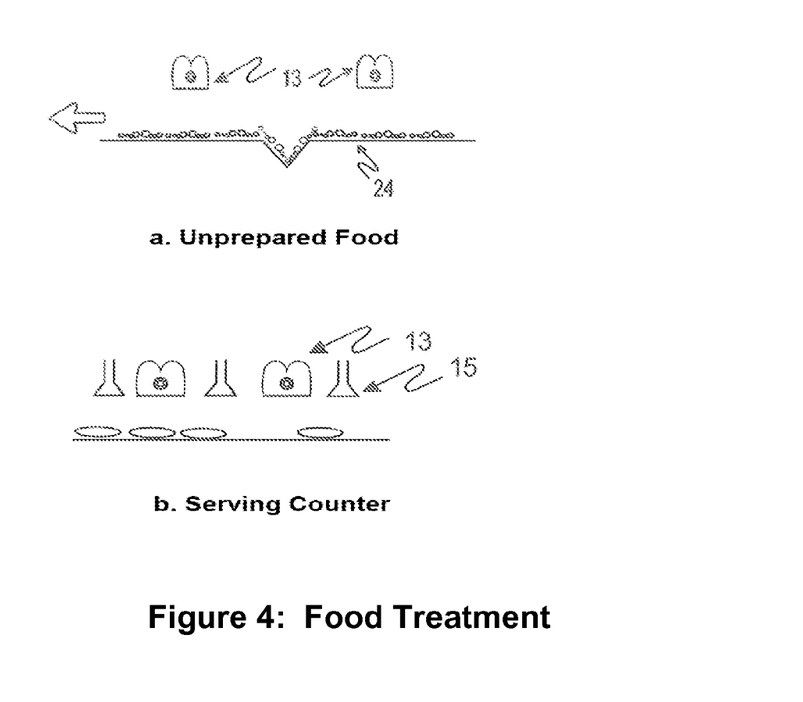
FIG. 4 is a perspective schematic view of a preferred embodiment of the present invention defining the location of important components for disinfecting food prior to handling by kitchen or cooks before serving therein.

FIG. 4a illustrates the NUV source(s) located above a conveyor that carries raw and unprepared food prior to kitchen preparation as well as industrial packaging assembly lines that carry products that require disinfection. The conveyor assembly 24 is designed to maximize the surface area exposed to the NUV source(s). In some cases, several sources 13 are required because the exposed surface of the food or product can not be changed to expose the entire surface during the illumination time of one NUV source. Tumblers or vibrators are typically used to change the orientation of the foodstuffs or parts as they move along the conveyor. However, a rotary tumbler similar to a cloth dryer with the NUV source located in the center would be the preferred embodiment for disinfecting leafy greens. FIG. 4b illustrates the NUV source(s) 13 located beside heat lamps 15 or other heating surfaces used to keep the food hot on a serving counter prior to being delivered from the kitchen to the customer. In another embodiment, the NUV source is used to irradiate cool or cold foods, so heat lamps 15 are not used.

Figure 5:
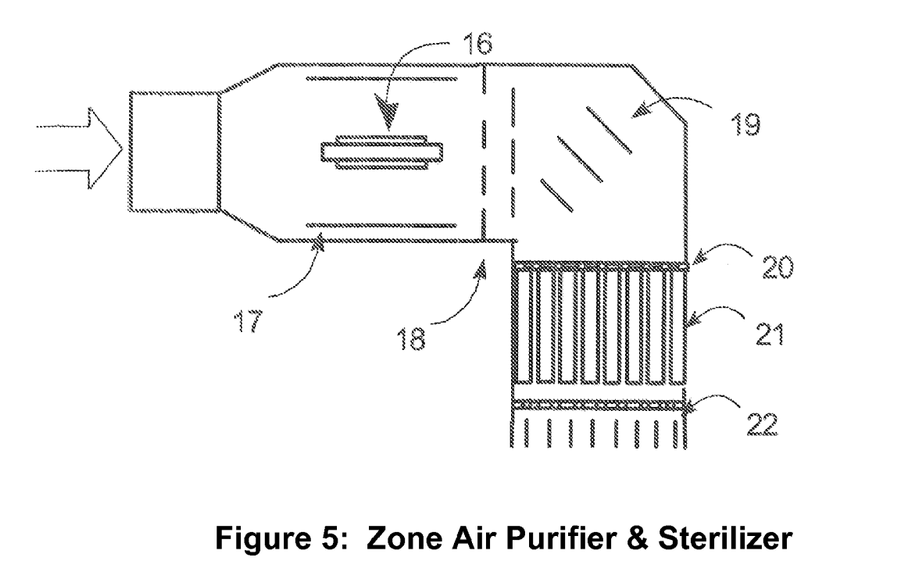
FIG. 5 is a perspective schematic view of a preferred embodiment of the present invention defining the location of important components for sterilizing air that is used to cover and protect the zone around a surgical operation or procedure independent of the location of the operation therein.

FIG. 5 illustrates the NUV source located inside an air sterilization apparatus that provides air for remote and separate operation tables. The NUV source 16 is located inside a UV reflector chamber 17 in order to reduce the loss of UV photons. A light trap 18 stops the UV light prior to the turning vanes 19 that direct the air flow vertically downward onto the operation site. A diffuser 20 ensures that the airflow is uniform across the duct. A high E field electrostatic precipitator (ESP) 21 follows the diffuser to remove particulates and reduce any ozone to oxygen. The airflow then passes through a second diffuser and humidifier 22 to ensure that the airflow is uniform across the duct and that the humidity level is controlled to some preset value.

Figure 6:
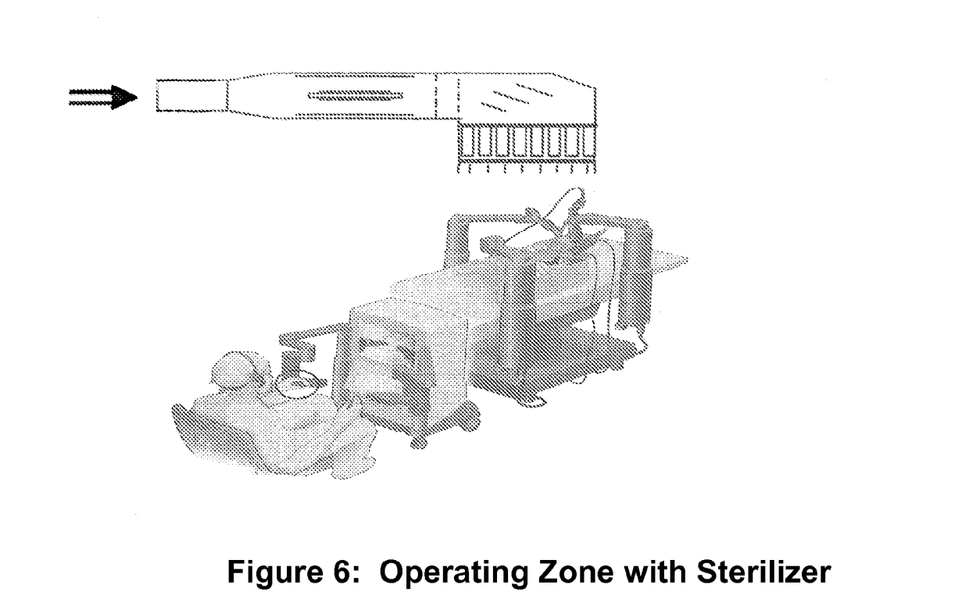
FIG. 6 is a perspective schematic view of a preferred embodiment of the present invention illustrating the zone air sterilization apparatus in conjunction with the remote protected operation zone therein.

FIG. 6 illustrates how the air sterilization apparatus would be used in conjunction with a remote operation site, where the doctor is using remote controlled surgical instruments that are inside the sterilized air zone.

Figure 7:
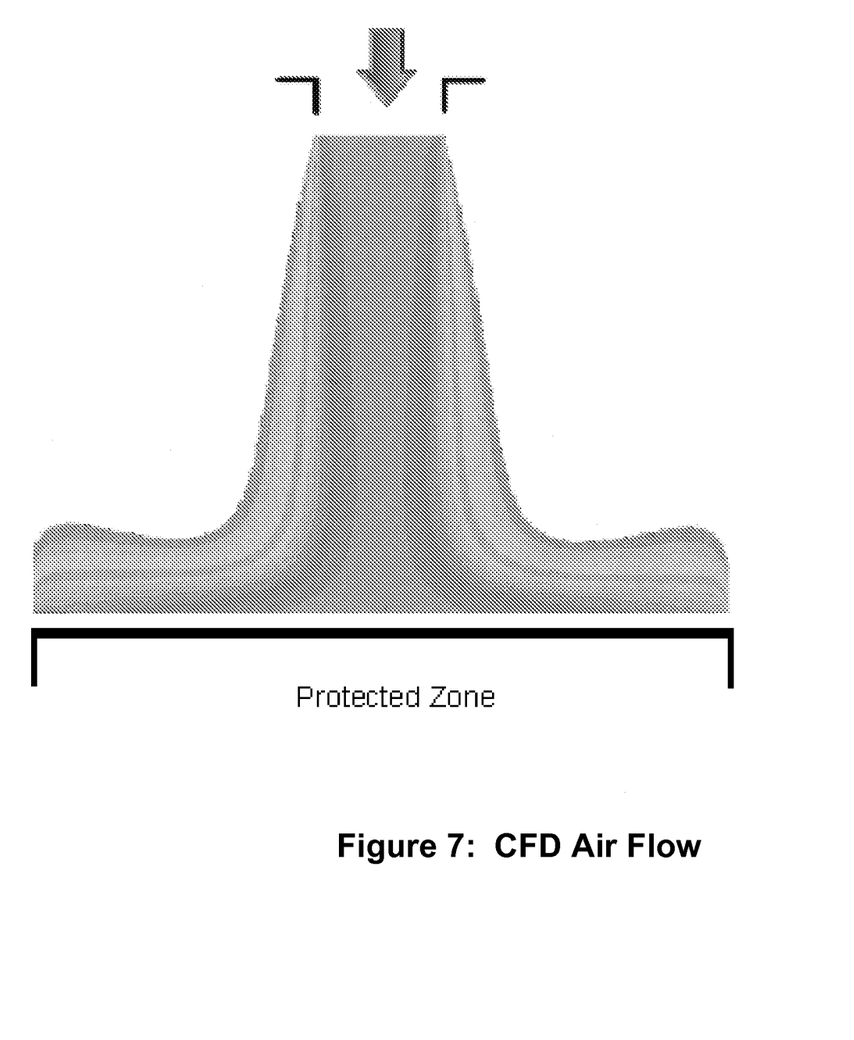
FIG. 7 is a CFD view of a preferred embodiment of the present invention defining the emitted airflow pattern from the sterilization apparatus that is used to cover and protect the zone around a surgical operation or procedure independent of the location of the operation therein.

FIG. 7 illustrates the airflow pattern using CFD computational fluidic design to ensure that the air above the operation zone is uniform and prohibits contaminated air from entering the protected zone.

FIGS. 8 through 15 are discussed in the technical and background sections of this specification.

Although the preferred embodiments of the present invention have been described herein, the above description is merely illustrative. Further modification of the invention herein disclosed will occur to those skilled in the respective arts. All such modifications are deemed to be within the scope of the invention as defined by the appended claims and not limited thereto.

What is claimed is:

1. A disinfecting apparatus comprising:
    a source of photons having a wavelength that substantially corresponds to an absorption peak of amino acids or proteins in microorganisms, the wavelength being 222 nm, the source of photons producing a quantity of ozone gas;
    a photon reflector secured in a spaced relationship to the photon source, whereby the apparatus produces photons that are directed to a selected zone or surface;
    an air duct surrounding the photon source;
    a particle removal means in the duct secured in a spaced relationship to the photon source; and
    wherein the particle removal means is an electrostatic precipitator positioned downstream of an air flow from the source of photons, and constructed and arranged to convert the quantity of ozone into oxygen gas.

2. The apparatus of claim 1, further comprising a humidifier in the air duct downstream of the electrostatic precipitator.

3. The apparatus of claim 2, further comprising a humidity sensor downstream of the humidifier.

4. The apparatus of claim 1, further comprising a light trap disposed between the photon source and the particle removal means.

5. The apparatus of claim 1, further comprising turning vanes within the duct to change the direction of airflow.

6. The apparatus of claim 1, further comprising a diffuser.

* * * * *

UNITED STATES PATENT AND TRADEMARK OFFICE
CERTIFICATE OF CORRECTION

PATENT NO. : 8,753,575 B2  
APPLICATION NO. : 11/831667  
DATED : June 17, 2014  
INVENTOR(S) : S. Edward Neister Page 1 of 1

It is certified that error appears in the above-identified patent and that said Letters Patent is hereby corrected as shown below:

On the Title Page, After Prior Publication Data, at Item (63) please insert:
--Related U.S. Application Data
Continuation-in-part of application No. PCT/US2006/003393, filed on Jan. 31, 2006.
Provisional application No. 60/593,626, filed on Jan. 31, 2005.--

Signed and Sealed this
Eleventh Day of November, 2014

Michelle K. Lee
*Deputy Director of the United States Patent and Trademark Office*